US005728086A

United States Patent [19]

[11] Patent Number: 5,728,086

[45] Date of Patent: Mar. 17, 1998

Niedospial, Jr.

[54] UNIVERSAL FLEXIBLE PLASTIC CONTAINER WITH MULTIPLE ACCESS PORTS

[75] Inventor: John J. Niedospial, Jr., Burlington, N.J.

[73] Assignee: Bracco Diagnostics, Inc., Princeton, N.J.

[21] Appl. No.: 688,401

[22] Filed: Jul. 30, 1996

[51] Int. Cl.[6] .......... A61B 19/00; A61M 5/00

[52] U.S. Cl. .......... 604/408; 604/403; 604/411; 604/262; 604/264

[58] Field of Search .......... 604/262, 264, 604/403, 408, 409, 411, 412, 413, 414, 415, 416

[56] References Cited

U.S. PATENT DOCUMENTS

| | | | |
|---|---|---|---|
| Re. 32,065 | 1/1986 | Ralston et al. . | |
| 331,039 | 11/1885 | Davis | 604/262 |
| 3,342,179 | 9/1967 | Ellmann | 604/408 |
| 4,088,166 | 5/1978 | Miller . | |
| 4,892,537 | 1/1990 | Carmen et al. . | |
| 4,976,707 | 12/1990 | Bodicky et al. . | |
| 4,978,579 | 12/1990 | Rosenbaum | 424/483 |
| 5,088,994 | 2/1992 | Porat . | |
| 5,289,858 | 3/1994 | Grabenkort | 604/411 |
| 5,385,564 | 1/1995 | Slater et al. | 604/403 |
| 5,423,794 | 6/1995 | Adolf et al. . | |

*Primary Examiner*—John G. Weiss
*Assistant Examiner*—David J. Cho
*Attorney, Agent, or Firm*—Imre Balogh

[57] ABSTRACT

Universal, flexible container with multiple access ports having first and second polymeric sheets, portions of which are embossed, superimposed on each other and sealed together at their periphery defining an interior reservoir with a bottom having a first and second angle of from 5° to 45° each from the center of the bottom and relative to a horizontal plane crossing the center of the bottom portion;

- a first access member at the center of the bottom portion equipped with tubing means and one-way her slip stopcock;
- a needle access member located on one side of the first access member; and
- a spike access member located on the other side of the first access member.

31 Claims, 10 Drawing Sheets

UNIVERSAL FLEXIBLE PLASTIC CONTAINER WITH MULTIPLE ACCESS PORTS

BACKGROUND OF THE INVENTION

1. Field of the Invention

This invention relates to flexible plastic containers, such as bags and bottles, for the containment and delivery of fluids. More particularly, the invention relates to flexible plastic containers with multiple access ports for the containment and delivery of parenteral solutions including diagnostic contrast media, nutrients and drug formulations.

2. Reported Developments

Prior to the discovery and development of polymeric materials, parenteral liquids have been supplied to hospitals exclusively in glass bottles. The disadvantages of glass bottles, such as cost, shipping, storage and disposal, prompted the prior art to provide flexible, sterilizable containers in the forms of bags and bottles for the containment and delivery of parenteral solutions, such as diagnostic contrast media, nutritional and drug formulations. Such containers typically comprise: a flexible plastic sheet formed into a pouch, bag or bottle shape filled with a solution inside therein in a sterile environment; and one or more ports to fill and/or access the solution. Flexible tubing is also provided one end of which is connectable to a port on the container, and the other end connectable to a syringe or catheter pre-inserted into the site of delivery on the patient. Control means are also usually included with the tubing, such as valves and clamps for initiating, controlling and terminating the flow of the liquid to the delivery site. The container, tubing and control means are sterile packaged ready for use.

The prior art containers for medical applications are equipped with a single access port designed to deliver the medical fluids therefrom through an intravenous (IV) line, a spike or a needle. Accordingly, the containers are dedicated to one of these modes of delivery, thereby restricting medical personnel to adapt to a single mode of delivery built into the container rather than adapting the container to the mode of delivery best suited to particular circumstances in patient treatment. It would be desirable, especially in an emergency situation, to have available pre-filled medical containers the contents of which could be accessed by any mode of delivery.

Another requirement to be satisfied in flexible containers for elivering parenteral solutions to patients is that by their construction and design they deliver their total contents in a uniform, steady manner and without retaining liquid drops on their walls. By meeting such requirement the medical practitioner can determine the amount of parenteral solution delivered from the container to the patient. The prior art has addressed this requirement, as shown for example in U.S. Pat. No. 4,892,537, which discloses a bag having substantially parallel major sides or edges and converging minor sides which meet at a point forming an obtuse angle of at least 110°. The converging edges are designed to guide the filled bag contents in a substantially unobstructed manner in a funnel-like fashion to an exit port.

U.S. Pat. No. 4,088,166 addresses the problem of incomplete and non-uniform collapse of parenteral solution containers. The incomplete collapse is attributed to the stiffness of the thin-walled polypropylene container which tends to resist collapse to such a degree that the moderate suction pressure exerted on the container by weight of the parenteral solution is insufficient to cause its complete collapse. The non-uniform collapse, on the other hand, is attributed to the observed facts that on some occasions, the bags collapse along the long axis of their cross section, while on other occasions they tend to collapse along both the short axis of the cross-section as well as the long axis. As a result, the medical practitioners cannot determine exactly how much parenteral solution has been delivered out from the container. In order to solve the problem of incomplete and non-uniform delivery, the patentee incorporates gusset portions in the body portion of the container adjacent the shoulder portion. The gusset portions include lines of flexing weakness to facilitate the collapse of the container adjacent the shoulder portion as the contents thereof are withdrawn. The gussets said to facilitate both the lateral and longitudinal collapse of the container as it is emptied.

Medical practitioners have also observed fluid "hold up", i.e., when drops of parenteral solutions tend to remain on the internal walls of the flexible container as the solution is being delivered to the site of administration. The moderate suction pressure exerted on the walls of the container is insufficient to overcome the force existing between the drops of liquid and the walls of the container. Often, as the container is being drained, the emptied portion of the parallel walls adhere to each other further trapping drops of the liquid. As a consequence, the prescribed amount of parenteral solution is not delivered to the patient. Such delivery, especially in traumatic circumstances where a precise amount of a drug must be delivered into the patient, can make the difference between life and death of the patient.

The present invention addresses the problems associated with the lack of complete delivery of content, such as incomplete and non-uniform collapse of the container during administration of the parenteral solution, and hold up of drops of the solution on the walls of the container. The present invention provides means by which the parallel walls of the container are spaced apart from each other by having all or at least portions of the wall embossed which, due to low coefficient of friction, allows relative movement of the walls and prevents sticking.

The present invention provides easy and varied access to the parenteral solution contained in the flexible container by having incorporated therein separate access ports for a needle, spike and needleless luer access and for bulk or gross dispensing.

The present invention also provides a unitary container having needleless luer access and IV line integral with the container requiring no assembly prior to use. Such a unitary container is especially suited for use in both hospital and field emergency situations where assembly of prior art devices, having a bag, tubing, extension tubing, needle and catheter are individually packaged in a kit, would require considerable time prior to use.

SUMMARY OF THE INVENTION

The present invention is directed to a universal, flexible, unitary plastic container, such as a bag, pouch or bottle, for the containment and delivery of parenteral solutions, such as diagnostic contrast media, nutrients and drug formulations to a patient in need of such parenteral solutions.

The universal, flexible container of the present invention may be of any configuration, such as square, round, oval, hexagonal or octagonal. Typically, it is a generally rectangular configuration which will be described hereunder.

The universal, flexible container of the present invention comprises:

a) first and second flexible plastic sheets having a generally rectangular configuration superimposed and sealed together at their periphery to form a pouch defining an interior, said pouch having a top and a bottom portion; said bottom portion terminates in a first angle and a second angle of from about 5° to about 45°, preferably of from about 10° to about 30°, and most preferable from 10° to 20° from the center of said bottom portion and relative to a horizontal plane crossing the center of said bottom portion to direct and facilitate the flow of content of the solution contained in the pouch towards the center of said bottom portion; all, or at least portions of said interior of said pouch being mechanically deformed to prevent adhesion of said first and second plastic sheets;

b) an IV access port integral with an IV line which is equipped with a one-way stopcock, vent and luer fitting with removable cap located in the center bottom portion of the pouch;

c) a needle access port located on one side of the IV access port in the bottom portion of the pouch; and d) a spike access port located on the other side of the IV access port in the bottom portion of the pouch;

said needle and spike access ports being equipped with crimp seals.

In one embodiment the one-way luer slip stopcock assembly with vent may be positioned at the open end of the IV line just below the removable cap. In another embodiment the one-way luer slip stopcock assembly with vent may be positioned adjacent to the IV access port.

Preferably the top portion at the periphery of the pouch comprises at least one hole for suspending the container when it is in use for delivering the content thereof to the delivery site.

Preferably the bottom portion at the periphery of the pouch comprises at least one, and preferably a plurality, of holes to facilitate suspending the container during the filling process.

Additional features and advantages of the present invention will be apparent from the drawings and of the detailed description.

a) a pouch with an IV access port located in the center, bottom portion of the pouch and an IV line, said IV line having a proximal end integral with the IV access port, and aa distal open end, said IV line is equipped with a one-way stopcock, vent and removable cap at the distal end of said IV line;

b) a needle access port located in the bottom portion of the pouch on one side of the IV access port; and c) a spike access port located in the bottom portion of the pouch on the other side of the IV access port.

Figure 2:
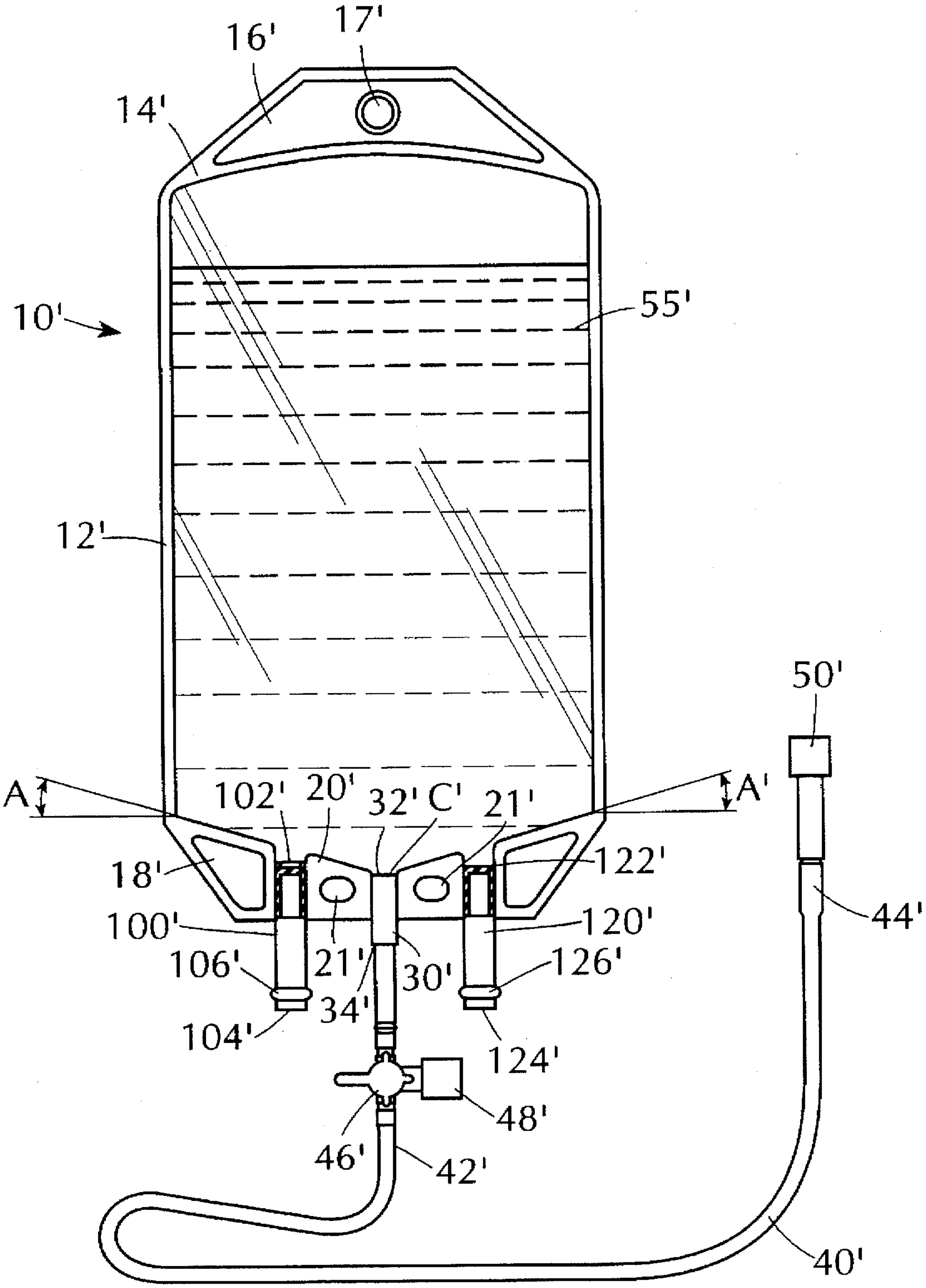

FIG. 2 is a plan view of another embodiment of the universal, flexible container in accordance with the present invention showing:

a) a pouch with an IV access port and an IV line, said IV line having a proximal end integral with the IV access port, and a distal end, said IV line is equipped with a one-way stopcock and a vent at the proximal end thereof adjacent to the IV access port, and a removable cap at the distal end thereof;

b) a needle access port located in the bottom portion of the pouch on one side of the IV access port; and c) a spike access port located in the bottom portion of the pouch on the other side of the IV access port.

Figure 1:
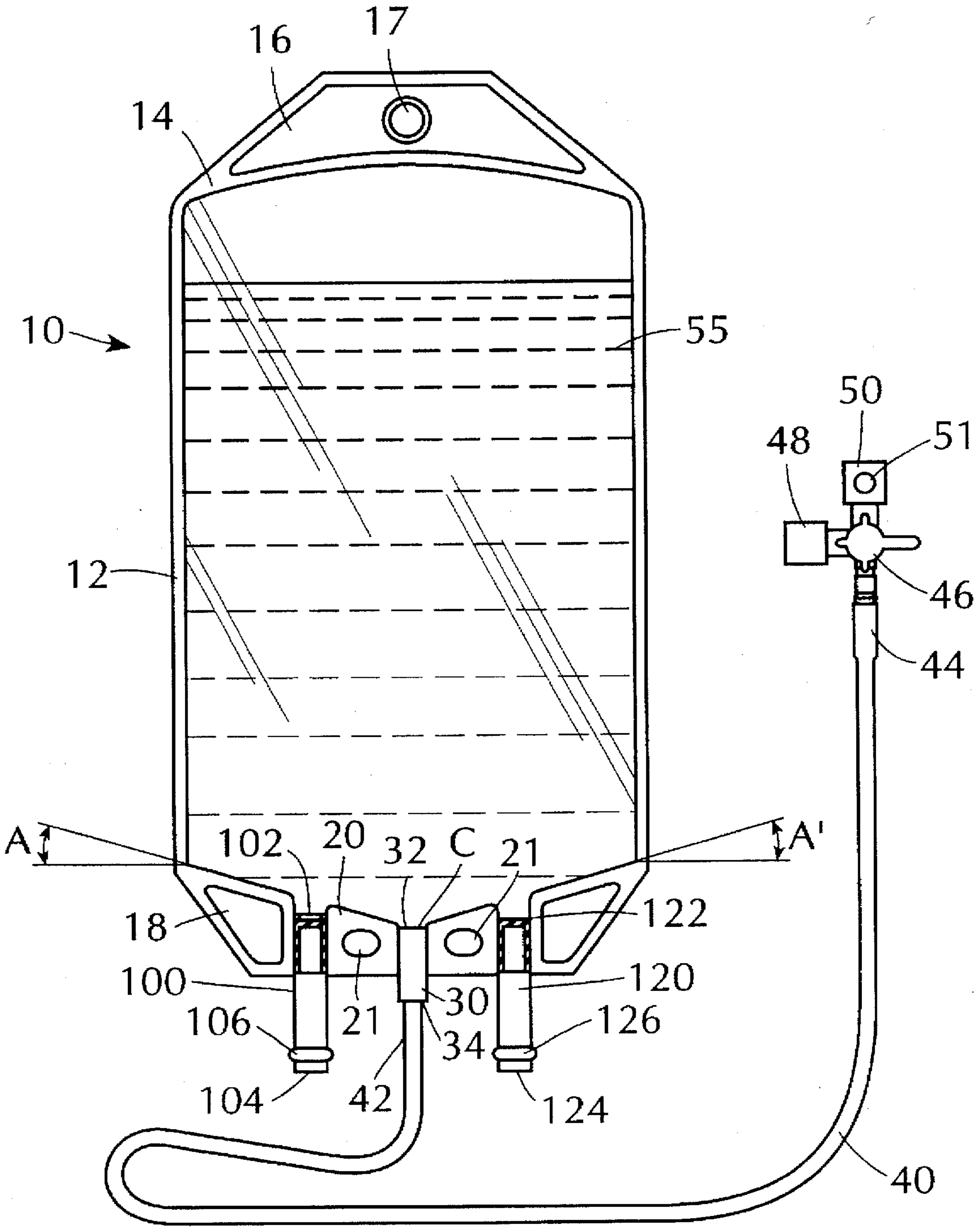
FIG. 1 is a plan view of a universal, flexible container in accordance with the present invention showing.
Figure 3A:
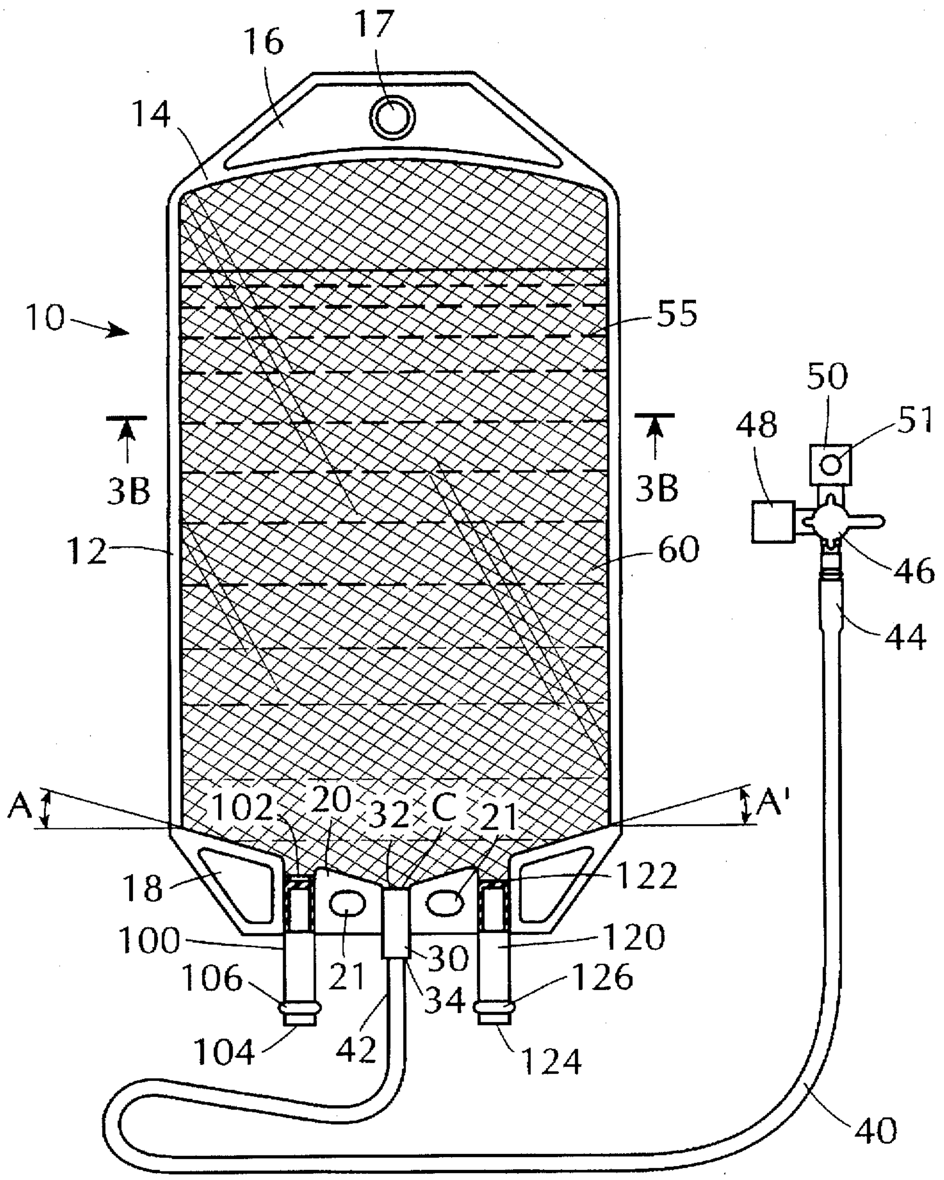
Figure 3B:
Figure 4A:
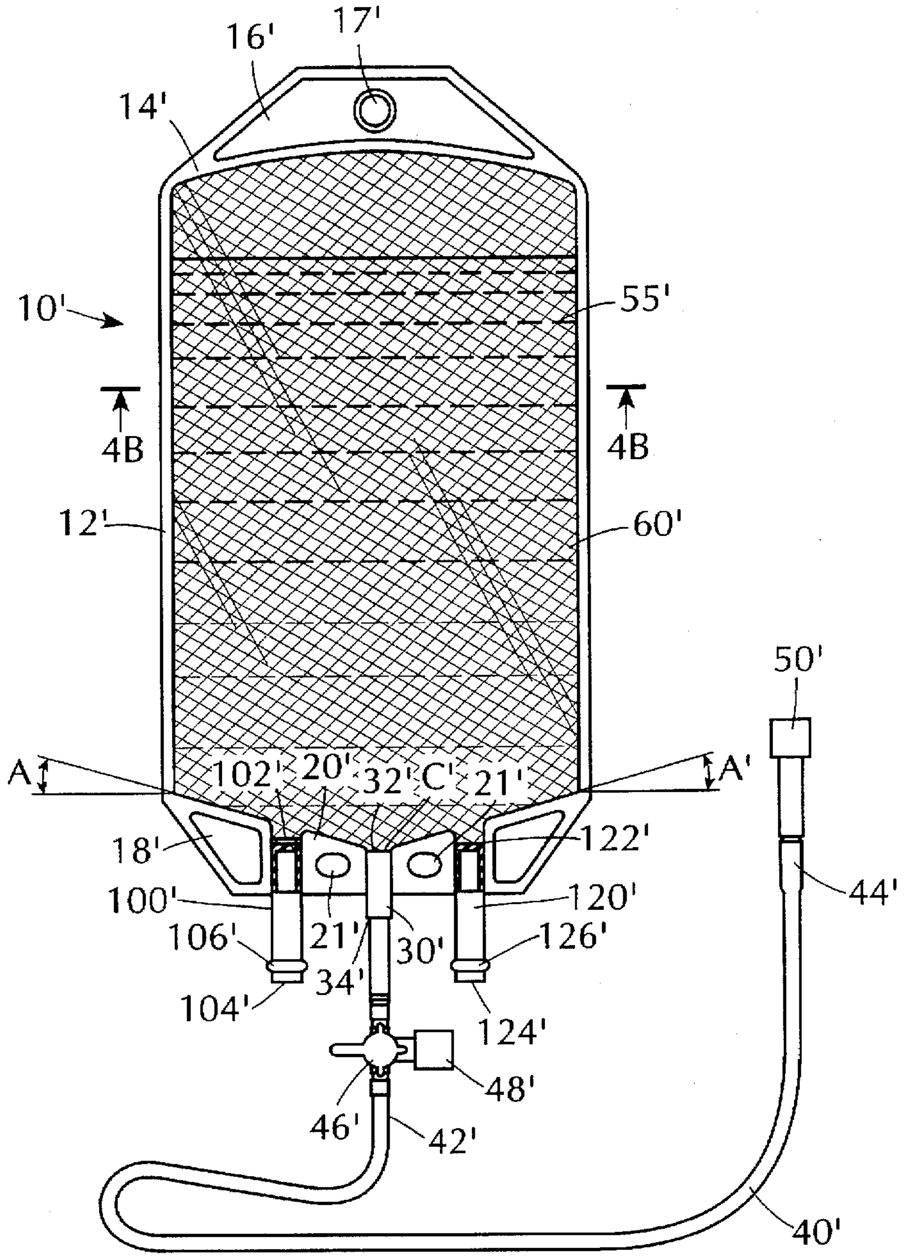
Figure 4B:
Figure 5A:
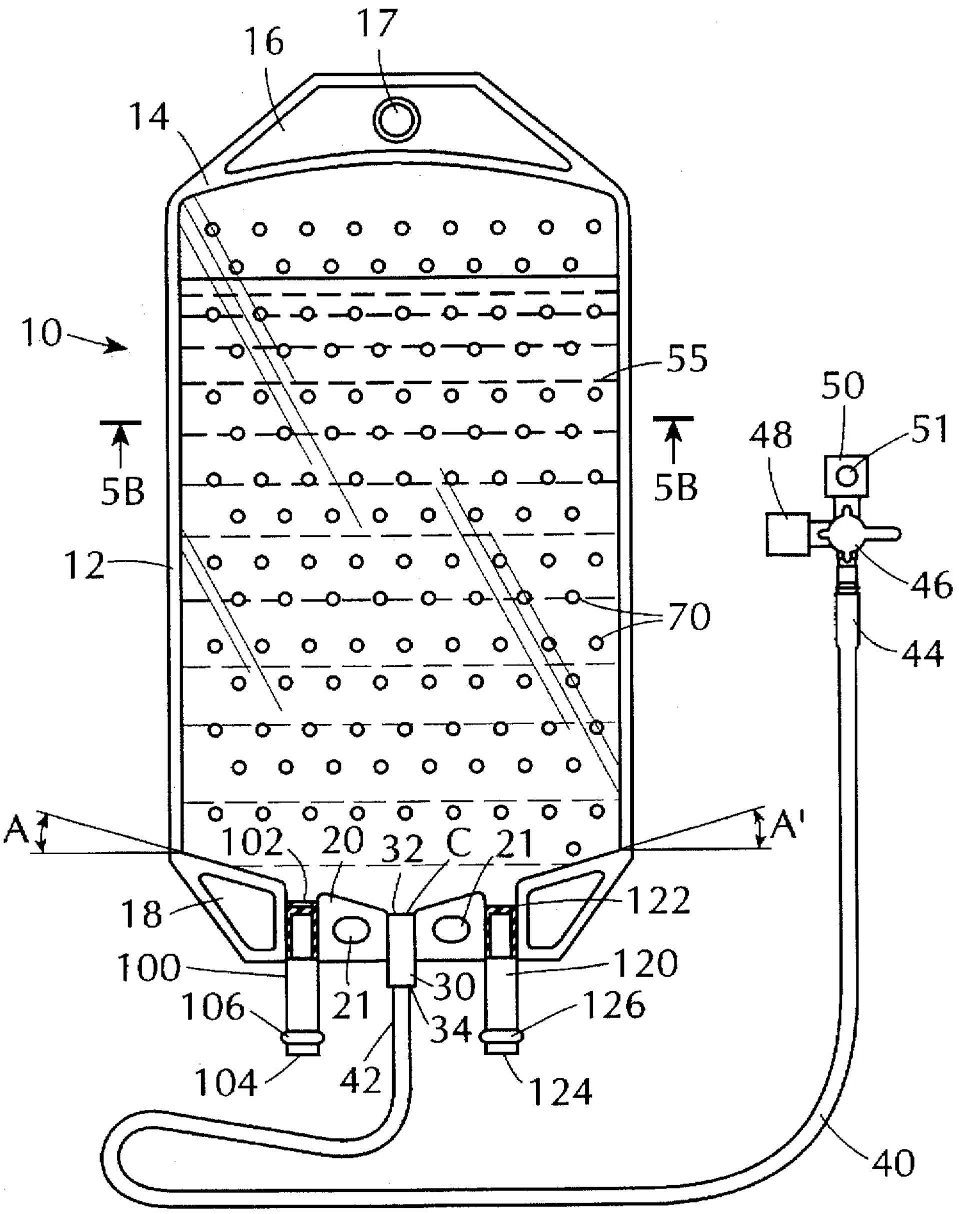
Figure 5B:
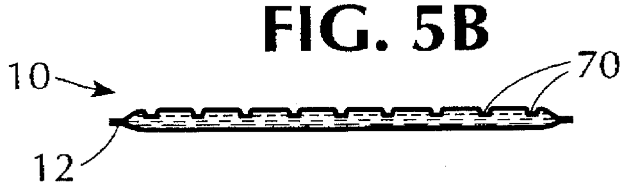
Figure 6A:
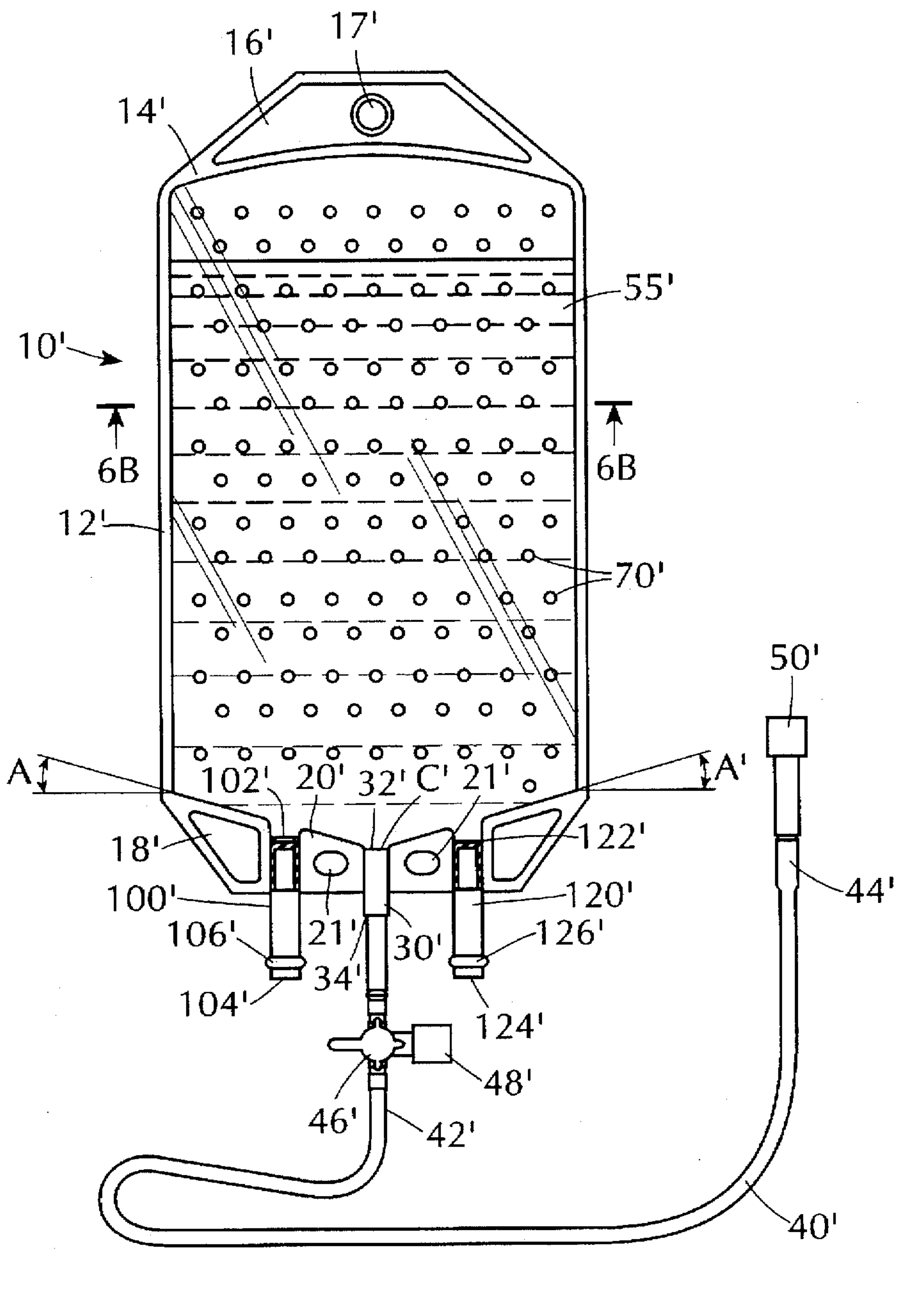
Figure 6B:
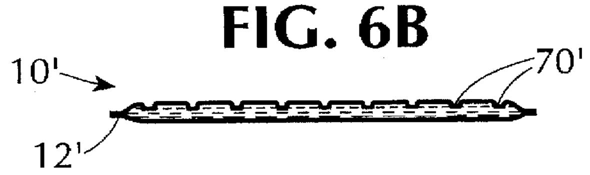
Figure 7A:
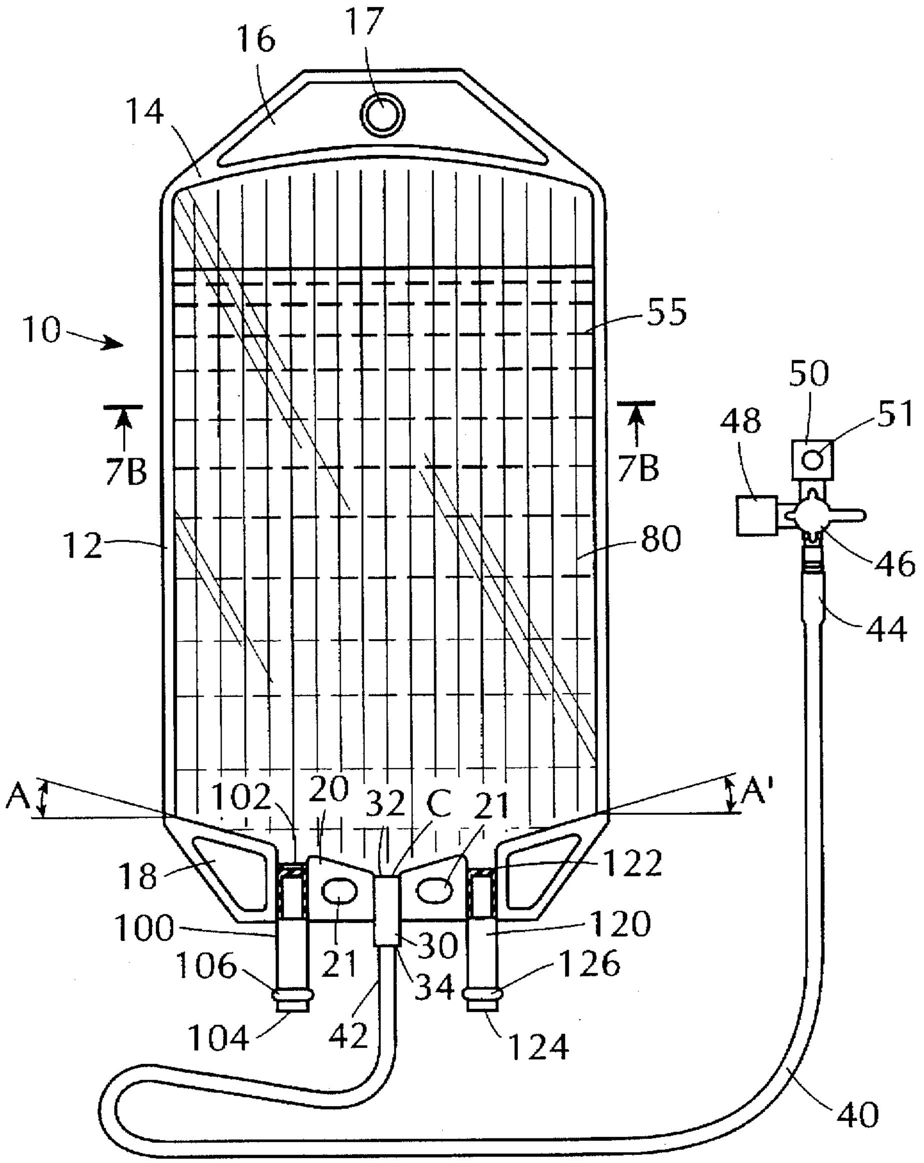
Figure 7B:
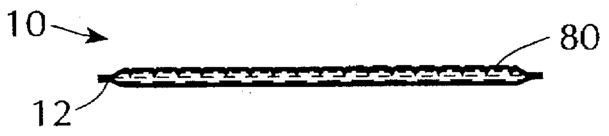
Figure 8A:
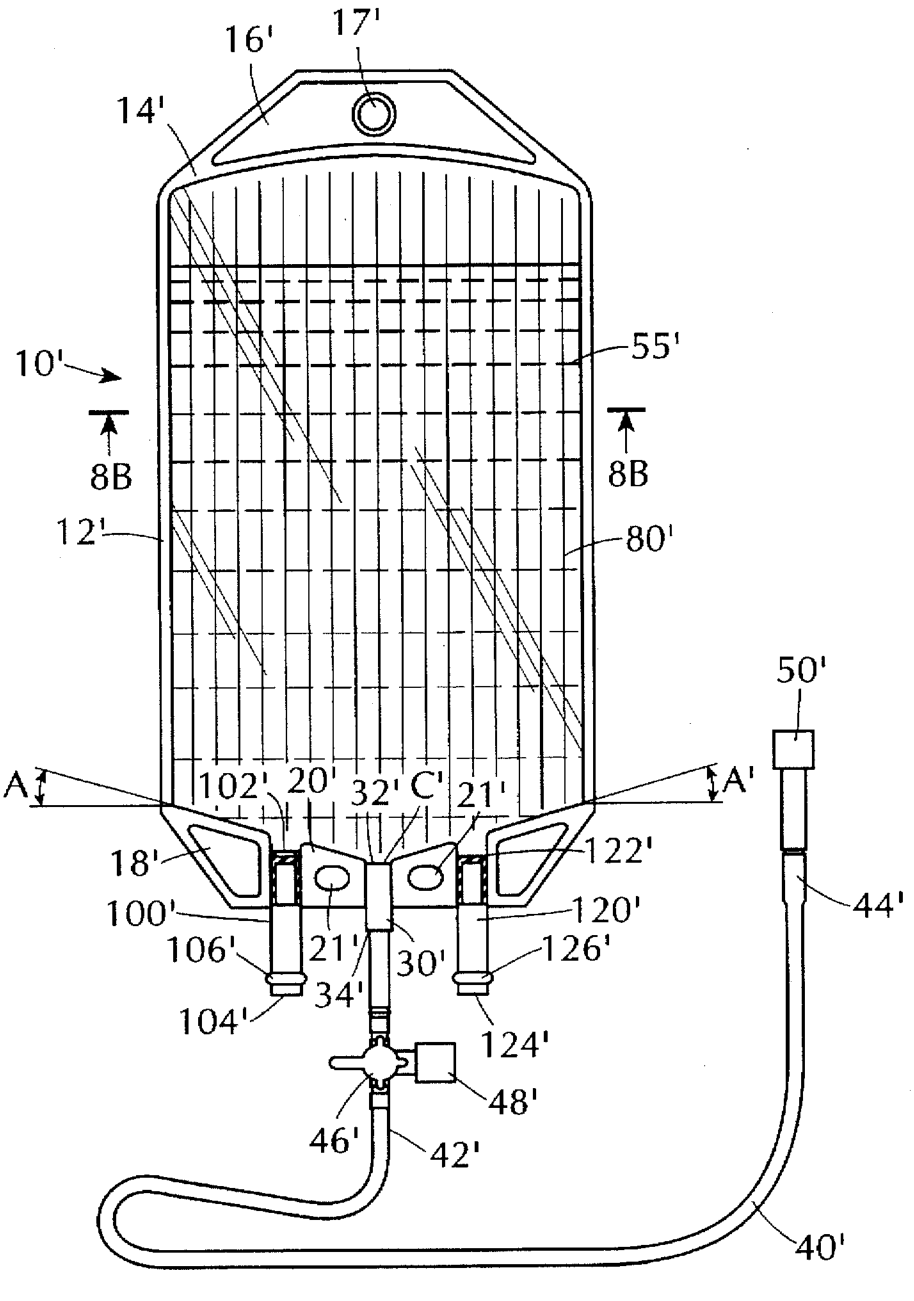
Figure 8B:
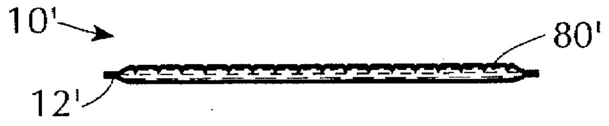
Figure 9A:
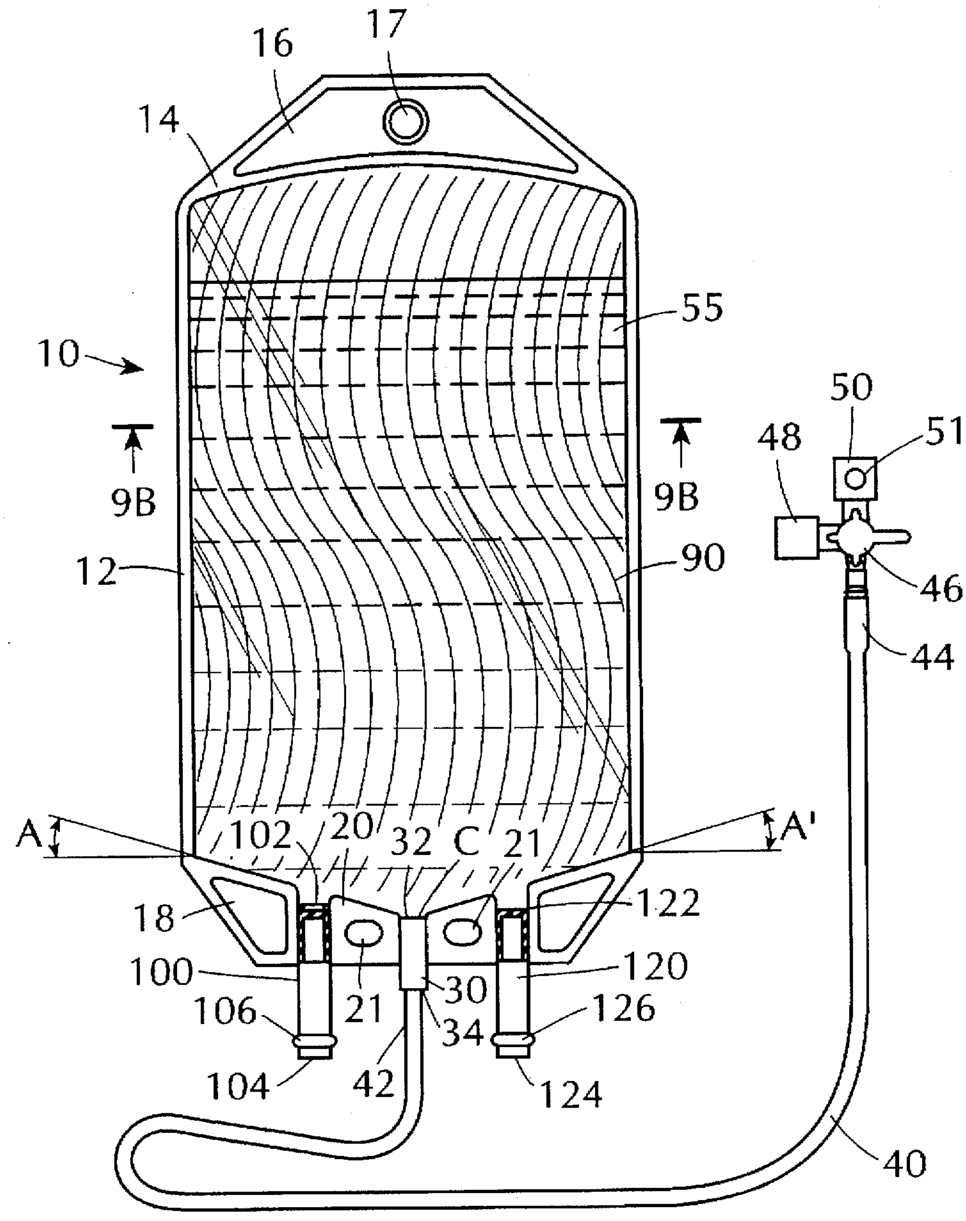
Figure 9B:
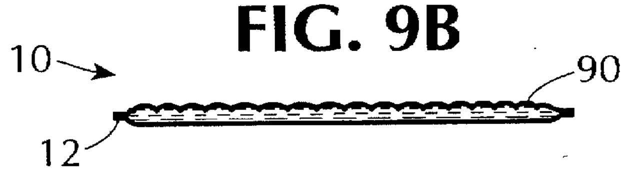
Figure 10A:
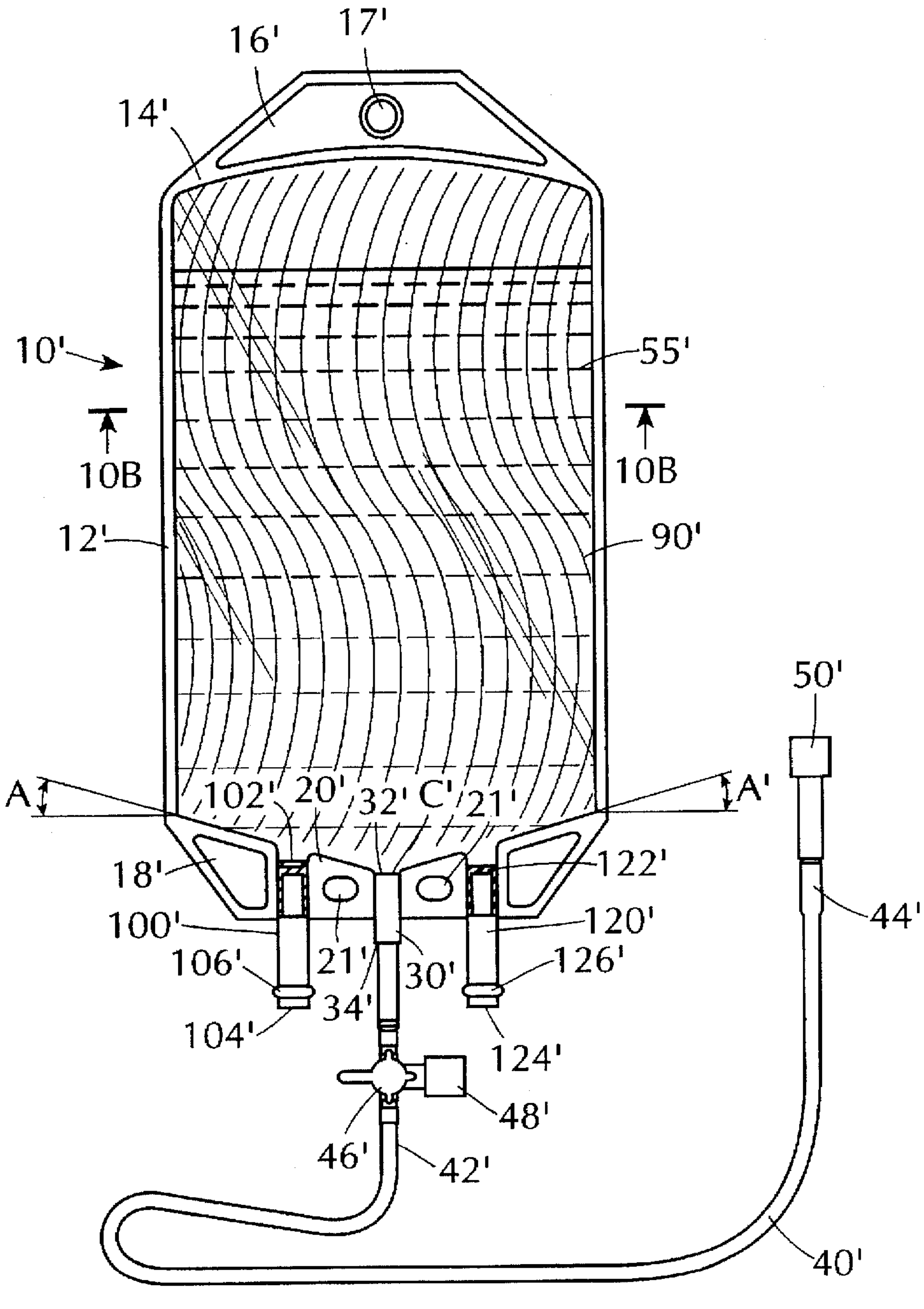
Figure 10B:

FIG. 3A is a plan view of the universal, flexible container shown in FIG. 1 one wall of which is embossed in a checkerboard fashion;

FIG. 3B is a cross-section of the universal, flexible container shown in FIG. 3A taken along the line 3B—3B;

FIG. 4A is a plan view of the universal, flexible container shown in FIG. 2 one wall of which is embossed in a checkerboard fashion;

FIG. 4B is a cross-section of the universal, flexible container shown in FIG. 4A taken along the line 4B—4B;

FIG. 5A is a plan view of the universal, flexible container shown in FIG. 1 one wall of which is embossed in a dotted fashion;

FIG. 5B is a cross-section of the universal, flexible container shown in FIG. 5A taken along the line 5B—5B;

FIG. 6A is a plan view of the universal, flexible container shown in FIG. 2 one wall of which is embossed in a dotted fashion;

FIG. 6B is a cross-section of the universal, flexible container shown in FIG. 6A taken along the line 6B—6B;

FIG. 7A is a plan view of the universal, flexible container shown in FIG. 1 one wall of which is embossed with vertically oriented channels;

FIG. 7B is a cross-section of the universal, flexible container shown in FIG. 7A taken along the line 7B—7B;

FIG. 8A is a plan view of the universal, flexible container shown in FIG. 2 one wall of which is embossed with vertically oriented channels;

FIG. 8B is a cross-section of the universal, flexible container shown in FIG. 8A taken along the line 8B—8B;

FIG. 9A is a plan view of the flexible container shown in FIG. 1 one wall of which is embossed with vertically oriented S-shape channels;

FIG. 9B is a cross-section of the universal, flexible container shown in FIG. 9A taken along the line 9B—9B;

FIG. 10A is a plan view of the universal, flexible container shown in FIG. 2 one wall of which is embossed with vertically oriented S-shape channels;

FIG. 10B is a cross-section of the universal, flexible container shown in FIG. 10A taken along the line 10B—10B;

DETAILED DESCRIPTION OF THE INVENTION

The present invention provides a universal, flexible plastic container, in the shape of a bag, pouch or bottle, for the containment and delivery of diagnostic contrast media, nutrients and drug formulations. In the drawings where like numerals indicate like elements or portions, the reference character 10 and 10' in FIGS. 1 and 2 indicate the container which, in a preferred embodiment, is a pouch-like device, comprising two superimposed sheets of suitable length and width made of flexible or pliable materials, such as polymeric materials including polyethylene, polypropylene, and preferably thermoplastic materials. The superimposed sheets forming the pouch-like container are preferably made of transparent materials so as to allow observation of the amount of its content during the filling operation and delivery thereof to the patient. Each of the superimposed transparent sheets is preferably formed of multilayers of laminated thin films at least one of which constitutes a barrier which is impervious to atmospheric gases, moisture and bacteria. The superimposed sheets are preferably flat welded to each other so as to form the pouch whose volume is zero before it is filled with a parenteral solution. When the pouch is filled or partially filled as shown by 55 in FIG. 1 and 55' in FIG. 2, it assumes the shape of a small cushion. The superimposed sheets are joined together along marginal areas 12, 12', 14, 14', 16, 16', 18, 18', 20 and 20' as shown in FIGS. 1 and 2 respectively.

Reference to embodiment of one of the present invention will be made by numerals without superscripts, while reference numerals with superscripts will relate to the second embodiment of the present invention.

The bottom portion of pouch 10 or 10' terminates in first angle A and second angle A' from the center C or C' of said bottom portion and relative to a horizontal plane crossing the center C or C' of said bottom portion to direct and facilitate the flow of content contained in the pouch towards an IV access port 30 or 30', needle access port 100 or 100', and spike access port 120 or 120'. Angles A and A' are of from about 5° to about 45°, preferably from 10° to 30° and most preferably form 10° to 20°.

IV access port 30 or 30' located at center C or C' of the bottom portion of pouch 10 or 10' is sealed between the first sheet and second sheet of the pouch comprising a top, liquid-contacting portion 32 or 32' and a bottom portion 34 or 34' to which a flexible tubing 40 or 40' i.e. intravenous (IV) line is permanently or fixedly attached by heat sealing or by other means. Access port 30 or 30' serves for both the filling and for the delivery of the parenteral liquid. It is important that top portion 32 or 32' of access port 30 or 30' is located below a horizontal plane crossing the center C or C' of said bottom portion so that all the liquid content of the pouch can be drained into flexible tubing 40 or 40'.

Referring to FIG. 1, flexible tubing 40 is permanently or fixedly attached at its proximal end 42 to IV access port 30 while at its distal end 44 it is attached to a control means comprising: a one-way luer slip stopcock 46, vent 48, and cap 50.

In the other embodiment of the invention shown in FIG. 2, flexible tubing 40' is permanently or fixedly attached at its proximal end 42' to access port 30', while at its distal end 44' it is covered with removably attached cap 50'. In this embodiment control means comprising a one-way luer slip stopcock 46' and vent 48', is located at proximal end 42' of flexible tubing 40', adjacent to IV access port 30'.

Marginal areas 16 and 16' in FIGS. 1 and 2 preferably comprise at least one hole 17 or 17' for suspending the pouch when it is in use for delivering the content of the pouch to a delivery site.

Marginal areas 20 and 20' in FIGS. 1 and 2 preferably comprise at least one, and more preferably a plurality, of hole(s) 21 and 21' to facilitate suspending the pouch during the filling process.

IV line 40 or 40' having its proximal end 42 or 42' integral with IV line port 30 or 30' may be fastened to the bottom portion of pouch 10 or 10' during manufacturing, just prior to filling the pouch or after the pouch is filled with the desired parenteral solution.

Referring to FIG. 1, the distal end 44 of IV line 40 has a one-way stopcock 46 with integral valve and luer slip or twist lock fitting, a cap 50 to cover the fitting in order to maintain sterility up to the point of use. The luer fitting on the one-way stopcock 46 provides a connection to a delivery site and allows the flow of content from the pouch 10 through the IV line 40 to the patient. The vent 48 may be positioned at the distal end 44 of IV line 40 or as an integral part of one-way stopcock 46. Based on the drug delivery procedure, the integral IV line may be configured with or without vent 48.

Referring to FIG. 2, the distal end 44' of IV line 40' has a cap 50' in order to maintain sterility up to the point of use. IV line 44' at its proximal end 42' has a one-way stopcock 46'. Luer slip or twist lock fitting is configured at the distal end 44' of the IV line 40 with or without vent 48'. As shown in FIG. 2, vent 48' is preferably positioned adjacent to one-way stopcock 46'.

Referring to FIGS. 1 and 2, on one side of the IV access port there is located needle access port 100 or 100', which is integral with pouch 10 or 10', sealed between the superimposed sheets at the time of manufacture of the pouch 10 or 10'. Needle access port 100 or 100', having proximal end 102 or 102' and distal end 104 or 104' is equipped at its distal end with crimp seal 106 or 106'. Access to the needle access port 100 or 100' using a steel needle is gained by severing crimp seal 106 or 106'.

On the other side of the access port there is located spike access port 120 or 120', which is also integral with pouch 10 or 10', sealed between the superimposed sheets at the time of manufacture of the pouch 10 or 10'. Spike access port 120 or 120', having proximal end 102 or 102', is equipped at its distal end with crimp seal 126 or 126'. Access to the spike access port 120 or 120', using a plastic spike, is gained by severing crimp seal 126 or 126'.

Needle access port 100 or 100' and spike access port 120 or 120' are positioned in the proximity of the IV access port, which positioning in combination with the bottom portion of pouch 10 or 10', having angle A or A', minimizes fluid waste/fluid hold up.

The container of the present invention may be used for delivering a single dose, multi-dose or a bulk of parenteral solution. The one-way stopcock serves as a means to control flow during sterilization, such as autoclaving, by preventing outward flow, and during drug delivery as required in multidose or bulk pack dispensing. The needle and spike ports, along with the IV access port, allow access to the drug in the pouch by means that happen to be available under any circumstances.

In addition to providing multiple access ports, the present invention provides further improvement in flexible containers designed for delivering parenteral solutions, such as diagnostic contrast media and drug formulations.

It was suprisingly discovered that if the inside wall of the first sheet or the second sheet forming the pouch 10 of FIG. 1 or pouch 10' of FIG. 2 is embossed, fluid hold up in the form of drops adhering to the inside walls can be reduced or eliminated and the walls, as the content of the pouch is being drained into the injection site, adhering together and further trapping drops of the fluid, can be prevented. In accordance with this discovery there are provided the following preferred embodiments of the invention.

Referring to FIG. 3A and FIG. 3B, the inside wall of first sheet of pouch 10 shown in FIG. 1 is embossed in a checkerboard manner 60, the checkerboard consisting of squares the 90° angles of which pointing downward towards the center C of the pouch. The size of the individual squares may be in the range of from 0.01 to 10 $mm^2$ or larger. The size of the individual squares may vary the determination of which would be influenced by the viscosity and the surface tension of the parenteral liquid for the delivery of which the pouch is intended.

While the inside wall of both first sheet and second sheet may be embossed, it was observed that the pouch functions better in terms of eliminating fluid hold up and preventing the superimposed walls from sticking together when only one inside wall of the first or second sheet is embossed.

FIG. 4A and FIG. 4B show the embodiment described in FIG. 2, except that the inside wall of first sheet of pouch 10' is embossed as described in FIG. 3.

Referring to FIG. 5A and FIG. 5B, the inside wall of first sheet of pouch 10 of FIG. 1 is embossed with dots or micro circles 70 in a spaced relationship from each other. The dots or circles may vary in diameter from 5 microns to several mms and may be spaced from each other of from about 10 microns to about 10 mms or longer. While both inside walls of the first sheet and second sheet may be embossed, it is preferred that only the first sheet or second sheet be embossed.

FIG. 6A and FIG. 6B show the embodiment described in FIG. 2, except that the inside wall of first sheet of pouch 10' is embossed 70' as described in FIG. 5.

Referring to FIG. 7A and FIG. 7B, the inside wall of first sheet of pouch 10 shown in FIG. 1 is embossed 80 in vertical channel configuration in spaced relationship from each other. The width of the individual channels may be in the range of from about 0.01 to about 10 mm or larger. The channels may be spaced from each other of from about 10 microns to about 10 mms. While both inside walls of the first sheet and second sheet may be embossed, it is preferred that only one inside wall of the first or second sheet be embossed.

FIG. 8A and FIG. 8B show the embodiment described in FIG. 2, except that the inside wall of first sheet of pouch 10' is embossed 80' as described in FIG. 7.

Referring to FIG. 9A and FIG. 9B, the inside wall of first sheet of pouch 10 of FIG. 1 is embossed 90 with vertically oriented channels which have a slight S-shape configuration in a spaced relationship from each other. The size of the width of individual channels may be in the range of from about 0.01 to about 10 mms or larger. The channels may be spaced from each other of from about 10 microns to about 10 mms. While both inside walls of the first sheet and second sheet may be embossed, it is preferred that only one inside wall of the first or second sheet be embossed.

FIG. 10A and FIG. 10B show the embodiment described in FIG. 2, except that the inside wall of first sheet of pouch 10' is embossed 90' as described in FIG. 9.

Materials Of Construction

The flexible container of the present invention is made of known polymeric materials having properties which make them suitable for sterile delivery of parenteral liquids. The sheets for forming the walls of the container are preferably multilayer sheets and characterized by heat resistance, gloss, strength, flexibility, and chemical inertness. Preferably the sheets are transparent or at least translucent enabling visual inspection of the contents at all times during delivery of content form the container to the patient. The container must be sterilizable, preferably by heat, along with its content. At least one layer of the sheet must be impervious to atmospheric gases and to steam. Preferably, the internal surface of the pouch in contact with the parenteral solution therein should be impervious to gas and steam. The interior layer in contact with the parenteral solution must not contain any toxic agents or even plasticizers which could leach out and contaminate the solution. The sheet may be made, for example, from polyvinylidene chloride sandwiched between two polyethylene or polyvinylacetate layers. The polyvinylidene chloride constitutes the impervious barrier. Further layers may be added to the face or back of the sheet, if desired, such as a polyolefin, preferably, polyethylene. Polyvinyl chloride is also suitable for the construction of the sheet and is well-accepted by the prior art for use in containers for medical fluid collection and delivery. Typical properties of polyvinyl chloride films include: a thickness of about 380 micron; a tensile strength of about 240 kg/cm$^2$; a moisture vapor transmission rate of about 14–20 (g/m$^2$/day at 38° C., 100% RH); and an oxygen barrier of 650 (cc/m$^2$/day at 23° C., 0% RH, bar. CRYOVAC® sterlizable medical films (W.R. Grace and Co.) are especially suitable to construct the sheets used in the present invention. The films comprise a polyethylene layer sandwiched between polyester outer layers sealed together by a modified propylene copolymer. Typical properties of the film include: a thickness of about 190 micron; a tensile strength of about 250 kg/cm$^2$; a moisture vapor transmission rate of 5 (g/m$^2$/day at 38° C., 100% RH); and an oxygen barrier of about 1500 (cc/m$^2$/day at 23° C., 0% RH, bar).

Other polymeric films or sheets constructing the universal, flexible container of the present invention include: copolyester ether monolayer films, such as polycyclohexanedimethylcyclohexane, dicarboxylate elastomer made by Eastman Kodak Co.; and ethyl vinyl acetate made by Stedim, Inc. It is important that the fluid contacting layer of the multilayer sheet contain no plasticizer which may contaminate the fluid content of the container. Preferably, no plasticizer should be used at all on any of the multilayers to form the universal, flexible container of the present invention.

The sheets used in the present invention may be embossed with the described configuration by techniques known in the art. Alternatively, the layer constituting the internal liquid contacting layer of the sheet may be embossed prior to forming the multilayer sheets.

Access ports and tubing used in the present invention may be made of polyvinyl chloride which are sold commercially for use in medical devices. Other port and tubing materials may also be used, such as CRYOVAC® Port Tubing (W.R. Grace & Co.) which comprise three concentric layers of polymeric materials: a polyolefin layer is sandwiched between an outer layer of modified propylene copolymer and an inner layer of ethylene vinyl acetate or polyvinyl chloride.

Process Of Making The Container

The flexible plastic container in the form of a bag, pouch or bottle is made of two rectangular sheets of polymeric materials one of which is embossed and flat welded together on four sides so as to define between the two sheets and the four welded sides a reservoir. The volume of the container is zero before it is filled and typically has an internal volume capacity of from about 50 to about 5,000 ml when it is filled with a medical fluid, such as a parenteral solution. Access ports 30 or 30', 102 or 102', and 122 or 122' are sealed by the same welding process used to seal the two superimposed layers of sheets together at the center C or C' of the container 10 or 10'. Upon completion of the welding process the container is suspended via holes 21 or 21', followed by filling the container through the IV access port with the desired medical fluid. Tubing 40 or 40' is then sealed to port 30 or 30' thereby making the container "ready for use". Alternatively, the container may be sealed by heat welding at its four edges except at its center portion C or C' and filled with the desired medical fluid prior to sealing the IV access port 30 or 30' between the superimposed sheets. In this alternative process, however, the port 30 or 30' and tubing 40 or 40' are welded together forming an integral access member comprising the port and tubing. With either process, the container of the present invention, when filled with the desired medical fluid, provides for instant delivery requiring no assembly of the container and access member.

In the process of delivering the medical fluid to a patient using the IV access port, the container 10 or 10' is suspended via hole 17 or 17', cap 50 or 50' is removed and a spike or similar means is engaged with end of tubing 40 or 40'. One way luer slip stopcock assembly is turned to open position thereby starting the flow of medical fluid from the container through the tubing and spike to the site of delivery on the patient. Vent 48 or 48' allows outside air to replace the drained medical fluid in the container so that fluid flow is steady and continuous. If discontinuation of fluid flow is desired, the one-way luer stopcock assembly is turned to the stop position. If fluid delivery is desired using the needle or spike access ports, the container is suspended via hole 17 or 17', crimp seal 106 or 126 is severed and needle or spike is inserted into the respective ports to enable delivery of the medical fluid to the desired site on the patient.

Various modifications of the several embodiments disclosed will become apparent. This invention is intended to include such modifications to be limited only by the scope of the claims.

What is claimed is:

1. A universal, flexible container with multiple access ports made of a polymeric material for the containment and delivery of medical fluid comprising:

a) first and second polymeric sheets having a square, round, oval, hexagonal, octagonal or rectangular configuration superimposed and sealed together at their periphery defining an interior reservoir, said container having a top portion and a bottom portion; said bottom portion terminates in a first angle and a second angle of from about 5° to about 45° each from the center thereof and relative to a horizontal plane crossing the center of said bottom portion; wherein the first and second polymeric sheets are made of polyvinylidene chloride sandwiched between two layers of polyethylene or polyvinylacetate;

portions of said interior reservoir being mechanically or chemically embossed to maintain the polymeric sheets forming said interior reservoir spaced apart from each other thereby allowing relative movements of said polymeric sheets and preventing sticking therebetween;

b) a first access member integral with said container located at the center of said bottom portion allowing filling of the container with a medical fluid and access thereto for delivery to a patient, said access member comprising:

an access port located below the bottom portion of said container where said first angle and said second angle meet;

a flexible tubing having first end and second end, said first end is integral with said access port and said second end is removably covered with a cap, said flexible tubing equipped with a one-way luer slip stopcock assembly with a vent for controlling the delivery of the medical fluid from the container;

c) a second access member comprising a needle access port located on one side and adjacent to said first access member in the bottom portion of said container; and d) a third access member comprising a spike access port located on the other side and adjacent to said first access member in the bottom portion of said container, said needle and spike access ports being equipped with crimp seals to maintain the medical fluid in said interior reservoir.

2. The universal, flexible container of claim 1, wherein said one-way luer slip stopcock assembly is located at said second end of said flexible tubing adjacent to said cap.

3. The universal, flexible container of claim 2 wherein the interior wall of said first sheet is embossed in a checkerboard fashion.

4. The universal flexible container of claim 3 wherein a 90° angle defined by said individual squares of said checkerboard points downward towards the access port of the container.

5. The universal, flexible container of claim 2 wherein the interior wall of said first sheet is embossed with micro circles or dots.

6. The universal, flexible container of claim 5 wherein said micro circles or dots have a diameter of at least 5 microns and are spaced from each other of form about 10 microns to about 10 millimeters.

7. The universal, flexible container of claim 2 wherein the interior wall of said first sheet is embossed with vertical channels in spaced relationship from each other oriented in a length-wise direction of the container.

8. The universal, flexible container of claim 7 wherein the width of each of said channels is of from about 0.01 to about 10 millimeters spaced from each other of from about 10 microns to about 10 millimeters.

9. The universal, flexible container of claim 2 wherein the interior wall of said first sheet is embossed with vertically oriented S-shaped channels in spaced relationship from each other oriented in a length-wise direction.

10. The universal, flexible container of claim 9 wherein the width of each of said S-shape channel is of from about 0.01 to about 10 millimeters spaced from each other of from about 10 microns to about 10 millimeters.

11. The universal, flexible container of claim 2 wherein said bottom portion terminates in a first and a second angle of from about 10° to about 30° each from the center thereof and relative to a horizontal plane crossing the center of said bottom portion.

12. The universal, flexible container of claim 2 wherein said bottom portion terminates in a first and a second angle of from about 10° to about 20° each from the center thereof and relative to a horizontal plane crossing the center of said bottom portion.

13. The universal, flexible container of claim 2 wherein said container further comprises at its top portion a heat welded periphery housing a hole therein for suspending said container during the filling process.

14. The universal, flexible container of claim 2 wherein said container further comprises at its bottom portion a heat welded periphery having a plurality of holes therein for suspending said container during delivery of content to the patient.

15. The universal, flexible container of claim 1, wherein said one-way luer slip stopcock assembly is located at said first end of said flexible tubing adjacent to said access port.

16. The universal, flexible container of claim 15 wherein the interior wall of said first sheet is embossed in a checkerboard fashion.

17. The universal, flexible container of claim 16 wherein a 90° angle defined by said individual squares of said checkerboard points downward toward the access port of the container.

18. The universal, flexible container of claim 15 wherein the interior wall of said first sheet is embossed with micro circles or dots.

19. The universal, flexible container of claim 18 wherein said micro circles or dots have a diameter of at least 5 microns and are spaced from each other of from about 10 microns to about 10 millimeters.

20. The universal, flexible container of claim 15 wherein the interior wall of said first sheet is embossed with vertical channels in spaced relationship from each other oriented in a length-wise direction of the container.

21. The universal, flexible container of claim 20 wherein the width of each of said channels is of from about 0.01 to about 10 millimeters spaced from each other of from about 10 microns to about 10 millimeters.

22. The universal, flexible container of claim 15 wherein the interior wall of said first sheet is embossed with vertically oriented S-shape channels in spaced relationship from each other oriented in a length-wise direction.

23. The universal, flexible container of claim 22 wherein the width of each of said S-shape channel is of from about 0.01 to about 10 millimeters spaced from each other of from about 10 microns to about 10 millimeters.

24. The universal, flexible container of claim 15 wherein said bottom portion terminates in a first and a second angle of from about 10° to about 30° each from the center thereof and relative to a horizontal plane crossing the center of said bottom portion.

25. The universal, flexible container of claim 15 wherein said bottom portion terminates in a first and a second angle of from about 10° to about 20° each from the center thereof and relative to a horizontal plane crossing the center of said bottom portion.

26. The universal, flexible container of claim 15, wherein said container further comprises at its top portion a heat welded periphery housing a hole therein for suspending said container during the filling process.

27. The universal, flexible container of claim 15 wherein said container further comprises at its bottom portion a heat welded periphery housing a hole therein for suspending said container during the filling process.

28. The universal, flexible container of claim 1, wherein said first and second polymeric sheets are made of polyvinyl chloride.

29. The universal, flexible container of claim 1, wherein said first and second polymeric sheets are made of a polyethylene layer sandwiched between polyester outer layers sealed together by a propylene copolymer.

30. The universal, flexible container of claim 1, wherein said first and second polymeric sheets are made of polycyclohexanedimethylcyclohexane dicarboxylate.

31. The universal, flexible container of claim 1, wherein said first and second polymeric sheets are made of ethyl vinyl acetate.

* * * * *